United States Patent [19]

Murakami et al.

[11] 4,341,536
[45] Jul. 27, 1982

[54] METHOD FOR CONTINUOUSLY REMOVING FINE DUST PARTICLES FROM GASES

[75] Inventors: Fumiki Murakami, Otake; Minoru Ikeda, Hiroshima; Takashi Tokutomi; Toshiharu Nakano, both of Otake, all of Japan

[73] Assignee: Mitsubishi Rayon Company, Ltd., Tokyo, Japan

[21] Appl. No.: 224,435

[22] Filed: Jan. 12, 1981

Related U.S. Application Data

[63] Continuation of Ser. No. 77,270, Sep. 20, 1979, abandoned.

[30] Foreign Application Priority Data

Oct. 24, 1978 [JP] Japan ................................ 53-146166

[51] Int. Cl.³ .......................... B01D 47/02; B01D 47/12
[52] U.S. Cl. ............................................. 55/93; 55/95; 55/244; 261/112; 261/113
[58] Field of Search .................... 55/90, 93, 95, 240, 55/257MP, 244; 261/109, 110, 112, 113

[56] References Cited

U.S. PATENT DOCUMENTS

| | | | |
|---|---|---|---|
| 432,055 | 7/1890 | Learmonth | 261/109 |
| 2,862,696 | 12/1958 | Zuiderweg et al. | 261/113 |
| 2,947,112 | 8/1960 | Morrison | 261/110 |
| 3,656,280 | 4/1972 | Perry | 55/240 |
| 3,957,465 | 5/1976 | Pircon | 55/90 |
| 4,066,416 | 1/1978 | Panov et al. | 261/113 |
| 4,159,291 | 6/1979 | Bruckert et al. | 261/114 R |

FOREIGN PATENT DOCUMENTS

| | | | |
|---|---|---|---|
| 92879 | 9/1936 | Austria | 261/111 |
| 2001458 | 7/1971 | Fed. Rep. of Germany | 261/112 |
| 49893 | 6/1861 | France | 261/112 |

*Primary Examiner*—David L. Lacey
*Attorney, Agent, or Firm*—Oblon, Fisher, Spivak, McClelland & Maier

[57] ABSTRACT

A method for continuously removing fine dust from gases which contain them, consisting of: introducing the gas at a gas linear velocity of 10 to 80 m/sec and a liquid at a rate such that the liquid-to-gas ratio; L/G, is 1 to 50 l/m³, in parallel, into slit(s) or hole(s) which are set in tray(s) causing impingement onto a baffle plate which is set beneath the tray; and then carrying away the fine dust particles from the gas by the liquid, which is separated from the gas, is disclosed, along with apparatus to effectuate the process.

2 Claims, 7 Drawing Figures

METHOD FOR CONTINUOUSLY REMOVING FINE DUST PARTICLES FROM GASES

This is a continuation of application Ser. No. 077,270, filed Sept. 20, 1979, now abandoned.

BACKGROUND OF THE INVENTION

1. Field of the Invention

This invention relates to a method, and an apparatus for carrying out said method by continuously removing fine dust particles from gases.

2. Description of the Prior Art

Dust collectors have heretofore been employed equipped with a venturi scrubber, a jet scrubber or a glass wool to remove fine dust particles having sizes smaller than several tens of microns.

Gases obtained by the catalytic oxidation reaction in vapor phase, such as isobutylene, methacrolein, and the like contain fine dust particles of polymers of methacrylic acid and so on.

Such gases usually have a dust concentration of about 100 mg/m$^3$. A test for removing fine dust particles using a venturi scrubber and a jet scrubber revealed a maximum removal rate of 65%. When the test was continued for several days, the throat portions and conduits for exhausting the gases were adhered and clogged with solid matter, making it impossible to continue the operation.

A dust collector employing the glass wool was also tested using the same gas as used in the above test. The rate for removing dust particles was greater than 98%. However, the glass wool was loaded with the solid matter within short periods of time, making it difficult to continue the operation.

SUMMARY OF THE INVENTION

The object of this invention therefore is to provide a method which is free of the above-mentioned defects.

This invention involves apparatus for continuously removing fine dust particles from gases, comprising a single stage or a plurality stages of trays 5 having slit(s) or hole(s) 6, baffle plates 7 installed beneath the trays 5, and inlet ports for introducing a gas 1 containing fine dust particles and a washing water 2 in parallel onto said trays, wherein said gas and liquid are injected from said slit(s) or hole(s) and are caused to impinge upon the baffle plate.

DESCRIPTION OF THE PREFERRED EMBODIMENTS

Figure 1:
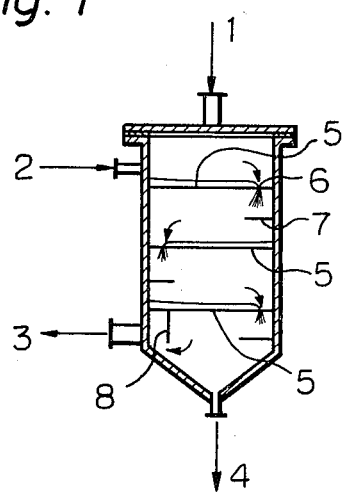
FIG. 1 is an elevational view showing an apparatus according to this invention.
Figure 2:
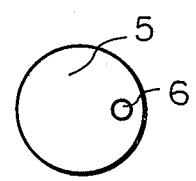
FIGS. 2, 3, 4 and 5 are plan views illustrating holes or slits formed in a tray.
Figure 3:
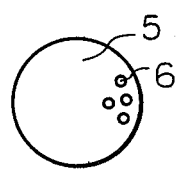
Figure 4:
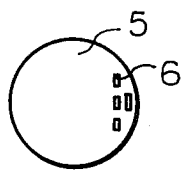
Figure 5:
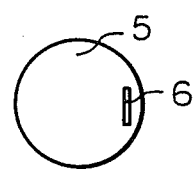
Figure 6:
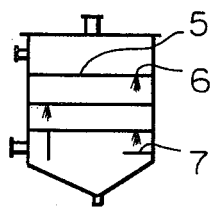
FIG. 6 is a side sectional view showing the apparatus of FIG. 1 but using trays as baffle plates.

The invention is mentioned below with reference to FIG. 1. Gases containing fine dust particles formed by the reaction in the gaseous phase and the washing water are supplied onto the tray of a first stage through inlet ports 1, 2. The gases and the liquid pass through a slit or a hole 6 at high speeds and hit the baffle plates 7 where fine dust particles are coagulated and are carried away by the liquid. The baffle plates 7 may be substituted by the lower trays as shown in FIG. 6. In putting the invention into practice, the tray, preferably, have a slit or a hole of such a size that the liquid-to-gas ratio L/G ranges from 1 to 50 l/m$^3$, and the gas linear velocity lies within a range of 10 to 80 m/sec.

The particles which are not removed by the tray of the first stage are removed in the second stage and in the third stage. The gases and liquid are exhausted through exhaust ports 3, 4. The trays may be installed in a single stage or in a plurality of stages depending upon the required rate for removing fine dust particles.

Using the apparatus equipped with three stages of trays, the dust was removed from the gas containing polymers of methacrylic acid. The rate of removal was greater than 95%. The operation was allowed to be continued for six months without causing clogging to the apparatus or the conduit.

Figure 7:
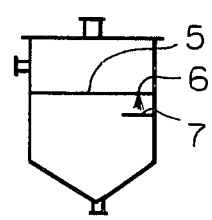
FIG. 7 is a side sectional view showing a single-stage apparatus.

FIGS. 2 to 5 show the arrangement of holes or slits formed in the tray. The number of the holes or slits will be suitably determined. FIG. 7 illustrates another embodiment of the apparatus of the invention employing a single stage of tray.

The apparatus of this invention is simple in construction as compared with the conventional apparatus, yet featuring very high rate of removing fine dust particles and enabling the treatment to be continuously performed.

EXAMPLE 1

A gas having a dust concentration of 100 mg/m$^3$, a temperature of 40° C. and a pressure of 0.8 kg/cm$^2$G was supplied at a rate of 5.5 m$^3$/hr, and the washing water was supplied at a rate of 38 l/hr into an apparatus having three stages of trays of a diameter of 60.5 mm each having a hole of a diameter of 8.3 mm, with the distance between the stages being 50 mm, and the distance between the baffle plate and the tray being 25 mm. The pressure loss between the inlet port and outlet port for the gas was 1200 mmH$_2$O, the particle concentration in the outlet gas was smaller than 5 mg/m$^3$, and the rate for removing fine dust particles from the inlet gas was greater than 95%. The operation was continued for six months. There was no clogging in the apparatus or in the conduits.

What is claimed is:

1. A method for continuously removing fine dust particles from gases which contain them, consisting essentially of:

introducing said gas and a liquid into a gas-liquid contact apparatus, said liquid being delivered to a tray(s) in said apparatus at a rate to form a liquid layer on said tray(s), directing said gas onto said liquid layer and then directing said gas and said liquid together in parallel at a high speed of a gas linear velocity of 10-80 m/sec and at a liquid-to-gas ratio of 1 to 50 l/m$^3$ through slit(s) or hole(s), which are located in the general plane of said tray(s) the slit(s) or hole(s) being sized so as to provide said gas linear velocity and said liquid-to-gas ratio, impinging the high speed mixture against a baffle plate having an imperforate section located directly beneath the slit(s) or hole(s) in order to coagulate said dust in said liquid, removing the liquid containing said coagulated dust and exhausting said gas having said coagulated dust removed therefrom.

2. The method of claim 1, wherein said contact apparatus has a multiple number of stages, defining said tray(s).

* * * * *